(12) United States Patent
Tchaga et al.

(10) Patent No.: US 7,294,614 B2
(45) Date of Patent: Nov. 13, 2007

(54) PHOSPHOPROTEIN AFFINITY RESINS AND METHODS FOR MAKING AND USING THE SAME

(75) Inventors: Grigoriy Simeonov Tchaga, Newark, CA (US); Rajinder K. Bhatia, Mountain View, CA (US)

(73) Assignee: Clontech Laboratories, Inc., Mountain View, CA (US)

( * ) Notice: Subject to any disclaimer, the term of this patent is extended or adjusted under 35 U.S.C. 154(b) by 0 days.

(21) Appl. No.: 11/249,151

(22) Filed: Oct. 11, 2005

(65) Prior Publication Data

US 2006/0079671 A1  Apr. 13, 2006

Related U.S. Application Data

(60) Provisional application No. 60/618,245, filed on Oct. 12, 2004.

(51) Int. Cl.
*C07H 13/00* (2006.01)
*A23J 7/00* (2006.01)

(52) U.S. Cl. .................. 514/2; 530/412; 530/416; 536/117; 536/112; 524/39

(58) Field of Classification Search ............... 530/233, 530/532, 209, 412, 416; 424/278.1; 514/2; 536/112, 117; 524/39
See application file for complete search history.

(56) References Cited

U.S. PATENT DOCUMENTS

| | | | |
|---|---|---|---|
| 4,569,794 A | | 2/1986 | Smith et al. |
| 5,047,513 A | | 9/1991 | Dobeli et al. |
| 5,284,933 A | | 2/1994 | Dobeli et al. |
| 5,310,663 A | | 5/1994 | Dobeli et al. |
| 5,594,115 A | | 1/1997 | Sharma |
| 5,962,641 A | * | 10/1999 | Nelson et al. ............... 530/344 |
| 5,990,289 A | | 11/1999 | Fauquex et al. |
| 6,242,581 B1 | | 6/2001 | Nelson et al. |
| 6,365,147 B1 | | 4/2002 | Luo et al. |
| 6,406,885 B1 | | 6/2002 | Stewart et al. |
| 6,479,274 B1 | | 11/2002 | Antalis et al. |
| 6,703,498 B2 | * | 3/2004 | Tchaga ........................ 536/112 |
| 2002/0019496 A1 | | 2/2002 | Pevow |
| 2002/0143158 A1 | * | 10/2002 | Perry et al. .................. 530/416 |
| 2006/0189797 A1 | * | 8/2006 | Songe et al. ................ 530/412 |

OTHER PUBLICATIONS

O'Brien et al. (1996) Non-porous magnetic chelator supports for protein recovery by immobilised metal affinity adsorption, J. Biotechnol. vol. 50, pp. 13-25.*

Ytrochimczuk et al. (2000) Modification of Malonamide Ion-Exchange/Chelating Resins Using the Fields—Kabatschnik Reaction and Their Application to Metal Ion Removal from Aqueous Solutions, J. Inorg. Organomet., vol. 10, No. 2, pp. 81-91.*

Zhang et al. (2000) Suitability of immobilized metal affinity chromatography for protein purification from canola. Biotechnol Bioeng. vol. 68, No. 1, pp. 52-58.*

Kramarenko et al. (1974) "Crystal structure of copper (II) iminodiacetate dihydrate", J. Struct. Chem. , vol. 14, No. 4, pp. 692-693.*

Hochuli et al. "New Metal Chelate Adsorbent Selective for Proteins and Peptides Containing Neighbouring Histidine Residues," Journal of Chromatography (1987) 411:177-184.

Mantovaara et al. "Purification of Human Serum Amyloid P Component (SAP) by Calcium Affinity Chromatography," Biotechnology and Applied Biochemistry (1989) 11:564-570.

Mantovaara et al. "Purification of Factor VIII:c Coagulant Activity from Rat Liver Nonparenchymal Cell Culture Medium by Immobilized Metal Ion Affinity Chromatography," Biotechnology and Applied Biochemistry (1991) 13:120-126.

Porath "Immobilized Metal Ion Affinity Chromatography," Protein Expression and Purification (1992) 3:263-281.

Chaga et al. "A New Method of Synthesizing Biopolymeric Affinity Ligands," Biotechnol. Appl. Biochem. (1997) 26:7-14.

Mantovaara et al. "Further Characterization of Carboxymethylated Aspartic Acid Agarose. Purification of Human $\alpha_2$ _Macroglobulin and Hemopexin," Biotechnology and Applied Biochemistry (1991) 13:371-379.

Mantovaara et al. "Carboxymethylated Aspartic Acid Agarose, a Selective Adsorbent for Calcium-Binding Proteins, Preliminary Studies," Biotechnology and Applied Biochemistry (1991) 13:315-322.

Porath et al. "Metal Chelate Affinity Chromatography, A New Approach to Protein Fractionation," Nature (1975) 258:598-599.

Chaga et al. "Immobilized Metal Ion Affinity Chromatography on $CO^{2+}$—Carboxymethylaspartate-Agarose Superflow, as Demonstrated by One-Step Purification of Lactate Dehydrogenase from Chicken Breast Muscle," Biotechnol. Appl. Biochem. (1999) 29:19-24.

(Continued)

*Primary Examiner*—Karen Cochrane Carlson
*Assistant Examiner*—Samuel Wei Liu
(74) *Attorney, Agent, or Firm*—Bret E. Field; Bozicevic, Field & Francis LLP; David C. Scherer (57) ABSTRACT

Phosphorylated protein (i.e., phosphoprotein) affinity resins and methods for making and using the same are provided. The subject resins include a substrate bonded to aspartate-based tetradentate ligand/metal ion complexes, where the tetradentate ligand/metal ion complexes have high specificity for phosphorylated amino acids. The subject resins find use in a variety of different applications, including phosphoprotein enrichment applications. Also provided are kits and systems that include the subject resins.

11 Claims, 2 Drawing Sheets

OTHER PUBLICATIONS

Chaga et al. "Natural Poly-Histidine Affinity Tag for Purification of Recombinant Proteins on Cobalt (II)-Carboxymethylaspartate Crosslinked Agarose," Journal of Chromotography A (1999) 864-247-256.

Porath et al. "Immobilized Metal Ion Affinity Adsorption and Immobilized Metal Ion Affinty Chromatography of Biomaterials. Serum Protein Affinities for Gel-Immobilized Iron and Nickel Ions," Biochemistry (1983) 22:1621-1630.

Stensballe et al. "Characterization of Phosphoproteins from Electrophoretic Gels by Nanoscale Fe(III) Affinity Chromatography with Off-Line Mass Spectrometry Analysis," Proteomics (2001) 1:207-222.

* cited by examiner

PHOSPHOPROTEIN AFFINITY RESINS AND METHODS FOR MAKING AND USING THE SAME

CROSS-REFERENCE To RELATED APPLICATIONS

Pursuant to 35 U.S.C. § 119 (e), this application claims priority to the filing date of U.S. Provisional Patent Application Ser. No. 60/618,245 filed Oct. 12, 2004; the disclosure of which is herein incorporated by reference.

INTRODUCTION

1. Background of the Invention

Signal transduction, transcriptional regulation, and cell division are just three examples of the many metabolic processes regulated by the phosphorylation and dephosphorylation of proteins by kinases and phosphatases. Despite the broad occurrence of phosphorylation in regulatory mechanisms, only a small percentage of all cellular proteins are phosphorylated at any given time. Accordingly, enrichment of the phosphorylated fraction may be necessary or desirable before starting an analysis, e.g., in order to reduce the background and increase the sensitivity of an assay. After enrichment, rare phosphoproteins may be less likely to escape detection.

In the past, many phosphorylated protein (i.e., phosphoprotein) enrichment methods have involved chemical modification of the phospho group followed by binding to a solid support. Disadvantages of such methods include alteration of the native protein structure, e.g., by the chemical modification, and lack of sufficient specificity for phosphorylated proteins.

Accordingly, there is continued interest in the development of new protocols for phosphorylated protein enrichment.

2. Relevant Literature

See U.S. Pat. Nos.: 4,569,794; 5,047,513; 5,284,933; 5,310,663; 5,962,641; 5,594,115; and 6,242,581 as well as Chaga et al., Biotechnol. Appl. Biochem. (1997) 26: 7-14. Also of interest are: Ford et al., Protein Expression and Purification (1991) 2:95-107; Hochuli, et al., J. Chromatography (1987) 411:177-184; Mantovaara et al., Biotechnology and Applied Biochemistry (1989) 11:564-570; Mantovaara et al., Biotechnology and Applied Biochemistry (1991) 13:315-322; Mantovaara et al., Biotechnology and Applied Biochemistry (1991) 13:120-126); Porath et al., Nature (1975) 258:598-599; Porath & Olin, Biochemistry (1983) 22:1621-1630; Porath, J., Protein Purification and Expression (1992) 3:263-281; Muszynska et al., J Chromatography (1992) 604:19-28; Andersson and Porath, Analytical Biochemistry (1986) 154: 250-254; Andersson, J Chromatography (1991) 539:327-334; Chaga et. al., Biotechnology and Applied Biochemistry (1989) 11:424-431 and Stensballe et al., Proteomics (2001),1:207-222. In addition, see: BD™ Phosphoprotein Enrichment Kit, Clontechniques, April 2003; BD TALON™ Metal Affinity Resins User Manual, PT1320-1 published Mar. 1, 2004 and BD™ Phosphoprotein Enrichment Kit User Manual, PT3731-1, published Jul. 7, 2003.

SUMMARY OF THE INVENTION

Phosphorylated protein (i.e., phosphoprotein) affinity resins and methods for making and using the same are provided. The subject resins include a substrate bonded to aspartate-based tetradentate ligand/metal ion complexes, where the tetradentate ligand/metal ion complexes have high specificity for phosphorylated amino acids. The subject resins find use in a variety of different applications, including phosphoprotein enrichment applications. Also provided are kits and systems that include the subject resins.

DEFINITIONS

Unless defined otherwise, all technical and scientific terms used herein have the same meaning as commonly understood by one of ordinary skill in the art to which this invention belongs. Still, certain elements are defined below for the sake of clarity and ease of reference.

The phrase "phosphoprotein affinity resin" refers to a composition of matter having a substrate bonded to aspartate-based tetradentate ligand/metal ion complexes that has affinity for phosphoproteins. The term "phosphoprotein" refers to a protein having one or more phosphorylated amino acid residues, e.g., one or more phosphorylated serine, threonine and/or tyrosine residues. As the resin includes an aspartate-based tetradentate ligand/metal ion complex, the resin is also referred to herein as an aspartate-based resin. By "aspartate-based tetradentate ligand" is meant a structure that is synthesized from an aspartic acid, e.g., L-aspartic acid, where the structure has four ligands capable of interacting with, i.e., chelating, a metal ion, such that the metal ion is stably but reversibly associated with the ligand, depending upon the environmental conditions of the ligand.

As is known in the art, resins may be charged or uncharged. A resin is charged when the ligands thereof are complexed with metal ions. Conversely, a resin is uncharged with the ligands thereof are uncomplexed or free of metal ions, but may be complexed with metal ions.

The phrase "metal ion source" refers to a composition of matter, typically a fluid composition, that includes metal ions.

As used herein, the term "contacting" means to bring or put together. As such, a first item is contacted with a second item when the two items are brought or put together, e.g., by touching them to each other.

The term "sample" as used herein refers to a fluid composition, where in certain embodiments the fluid composition is an aqueous composition.

As used herein, the phrase "in the presence of" means that an event occurs when an item is present. For example, if two components are mixed in the presence of a third component, all three components are mixed together.

The phrase "oxidation state" is used in its conventional sense, see e.g., Pauling, General Chemistry (Dover Publications, N.Y.) (1988).

A "dicarboxylic acid" is a small molecule having two separate carboxyl groups.

A "detergent" is a substance which has a nonpolar, hydrophobic part (avoids water) and a polar, hydrophilic part (attracted to water). Detergents may be ionic, e.g., cationic or anionic, or non-ionic, as is well known in the art.

DESCRIPTION OF THE SPECIFIC EMBODIMENTS

Phosphorylated protein (i.e. phosphoprotein) affinity resins and methods for making and using the same are provided. The subject resins include a substrate bonded to aspartate-based tetradentate ligand/metal ion complexes, where the tetradentate ligand/metal ion complexes have high specificity for phosphorylated amino acids. The subject resins find use in a variety of different applications, including phosphoprotein enrichment applications. Also provided are kits and systems that include the subject resins.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the subject invention provides phosphoprotein affinity resins, as well as methods for their preparation and use. In further describing the subject invention, the subject resins and their preparation are described first in greater detail, followed by a review of representative methods in which they find use. Also provided is a review of the kits and systems of the subject invention.

Phosphoprotein Affinity Compositions

As summarized above, the present invention provides phosphoprotein, affinity resins. The subject resins are characterized by having a substrate bonded to aspartate-based tetradentate ligand/metal ion complexes. By "aspartate-based tetradentate ligand" is meant a structure that is synthesized from an aspartic acid, e.g., L-aspartic acid, where the structure has four ligands capable of interacting with a metal ion. As such, by "tetradentate ligand" is meant that the ligand chelates a metal ion by occupying up to four, and typically four, coordination sites of a metal ion. For example, where a given metal ion has six coordination sites, four of them can be occupied simultaneously by the ligands of the subject tetradentate ligands.

In certain embodiments, the aspartate-based tetradentate ligand is an alkylaspartate ligand, generally a lower alkylaspartate ligand, such as 1 to 6, e.g., a 1 to 4, carbon atom alkylaspartate ligand, where the alkyl moiety may or may not be substituted. Representative alkylaspartate ligands of interest include, but are not limited to: carboxymethylated aspartate ligand, carboxyethylated aspartate ligand, etc.

As summarized above, the aspartate-based tetradentate ligand of the subject compositions is bonded to, either directly or through a linking group (also referred to herein as a spacer), a substrate or carrier matrix. Substrates of interest include, but are not limited to, cross-linked dextrans, polystyrenes, nylon, agarose, and polyacrylamides. Non-limiting examples of suitable, commercially available substrates include, but are not limited to, Sepharose®6B-CL (6% cross-linked agarose; Pharmacia); Superflow™ (6% cross-linked agarose; Sterogene Bioseparations, Inc.), Uniflow™ (4% cross-linked agarose; Sterogene Bioseparations, Inc.); silica matrices; magnetic beads and the like.

In the subject resins, the substrate component is bonded, optionally through a linking group, to the above summarized aspartate-based tetradentate ligand/metal ion complexes. In the subject compounds, the tetradentate ligands may be bonded, usually covalently bonded, to the carrier matrix or substrate either directly or through a linking group. Where linking groups are employed, such groups are chosen to provide for covalent attachment of the ligand to the substrate through the linking group. Linking groups of interest may vary widely depending on the nature of the substrate and ligand moieties. The linking group, when present, should preferably be biologically inert. A variety of linking groups are known to those of skill in the art and find use in the subject soluble metal ion chelating compounds. In many embodiments, the size of the linker group, when present, is generally at least about 50 daltons, usually at least about 100 daltons and may be as large as 1000 daltons or larger, but generally will not exceed about 500 daltons and usually will not exceed about 300 daltons. Generally, such linkers include a spacer group terminated at either end with a reactive functionality capable of covalently bonding to the substrate or ligand moieties. Spacer groups of interest include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylenediamine, terephthalic acid, 3,6-dioxaoctanedioic acid, ethylenediamine-N,N-diacetic acid, 1,1'-ethylenebis(5-oxo-3-pyrrolidinecarboxyylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject molecules include heterofunctional compounds, such as azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-maleimidobutyryloxysuccinimide ester, N-hydroxy sulfosuccinimidyl4-azidobenzoate, N-succinimidyl [4-azidophenyl]-1,3'-dithiopropionate, N-succinimidyl [4-iodoacetyl] aminobenzoate, glutaraldehyde, and succinimidyl 4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

The aspartate-based tetradentate ligands are typically bonded to the substrates at a ratio of tetradendate ligand to residue, e.g., glucose unit, that provides for acceptable characteristics, where the ratio of tetradentate ligand to polymeric residue often ranges from about 1 tetradentate ligand for every about 1 to 100 residues, e.g., from about 1 tetradentate ligand for every about 5 to 50 residues, including 1 tetradentate ligand for every about 10 to about 20 residues.

As reviewed above, the aspartate-based tetradentate ligands are complexed with metal ions. In other words, the tetradenate ligands are "charged with" metal ions. Said yet another way, in the subject resins metal ions are chelated by the tetradentate ligands of the resins.

A variety of different types of metal ions may be complexed to the ligands of the subject compounds. Metal ions of interest are those that have selective affinity for phosphorylated moieties. In certain embodiments, the metal ion is one that has a 3+ oxidation state. Specific representative metal ions of interest include, but are not limited to: hard metal ions, such as $Fe^{3+}$, $Al^{3+}$; lanthanides, including but not limited to: $Eu^{3+}$, $La^{3+}$, $Tb^{3+}$, $Yb^{3+}$, and the like. In certain embodiments, the metal ion of interest that is chelated by the ligand is $Fe^{3+}$. In certain embodiments, the metal ion of interest that is chelated by the ligand is $Eu^{3+}$. In certain embodiments, the resin includes a combination of metal ions, e.g., $Fe^{3+}$ and $Eu^{3+}$.

A feature of certain embodiments of the subject invention is that substantially all of the tetradentate ligand/metal ion complexes of a given resin have a metal ion complexed by all four ligands of a tetradentate ligand. In other words, in substantially all of the ligand/metal ion complexes of the resin, the metal ions are chelated by the tetradentate ligands by interactions with all four ligands, and not just three or two of the ligands. By "substantially all" is meant that, for a given resin having a given number of tetradentate ligands, of the tetradentate ligands that are complexed with a metal ion, at least about 85 number %, such as at about 90 number %, including at least about 95 number %, at least about 97 number %, at least about 99 number % or more, including 100 number % have the metal ion complexed to the tetradentate ligand by all four ligands.

In certain embodiments, the composition has the following structure:

wherein:

M=metal ion having a 3+ oxidation state;

$R_1$=a linking arm connecting the methylene carbon atom of the carboxymethyl group of CM-Asp with $R_2$;

$R_2$=a functional linking group that along with CM-Asp linking arm R1 is connected to $R_3$; and $R_3$=a substrate, which may have one or more additional residues bonded ligands of the same or different, but usually the same, structure.

Of particular interest in certain embodiments are the metal ion chelating compositions disclosed in U.S. Pat. Nos. 6,242,581 and 5,962,641 and U.S. patent application Ser. No. 09/920,684 published as US 2002/0019496; the disclosures of which are herein incorporated by reference, where the compositions described in these patents and applications are ones modified as described herein to be phosphoprotein specific.

The subject resins can be provided in the form of a chromatography column, e.g., wherein the resin is packed in a column. The resin can also comprise a structure that is a solid support of any shape or configuration. Thus, the resin can be in any form, e.g., a bead, a sheet, a well, and the like. Where the resin is a bead, the beads are provided in various sizes, depending, in part, on the nature of the sample being applied, where suitable bead sizes include from about 10 μm to about 500 μm, e.g., from about 10 μm to about 20 μm, from about 16 μm to about 24 μm, from about 20 μm to about 50 μm, from about 50 μm to about 100 μm, from about 60 μm to about 160 μm, from about 100 μm to about 200 μm, from about 100 μm to about 300 μm, from about 200 μm to about 300 μm, or from about 300 μm to about 500 μm. Non-limiting examples of formats in which a resin is provided include a gravity-flow column; a fast protein liquid chromatographic (FPLC) column; a multi-well (e.g., 96-well) column format; a spin column; and the like.

Methods of Fabrication

The subject resins may be prepared using any convenient protocol. In representative embodiments, an uncharged resin, e.g., as described above, is contacted with a source of metal ions in a manner such that metal ions are complexed by the tetredentate ligands to produce a charged resin. The uncharged aspartate-based resin may be one that is prepared using a variety of different protocols. Methods of preparing a variety of uncharged aspartate-based resins are reviewed in U.S. Pat. Nos. U.S. Pat. Nos. 6,242,581 and 5,962,641; the disclosures of which are herein incorporated by reference.

In producing the subject resins, the initial uncharged aspartate-based resin is charged with a metal ion in a manner the produces a phosphoprotein specific affinity resin. To charge the uncharged resin with metal ion, the uncharged resin is contacted with a source of metal ions in the presence of acetic acid. Typically, the source of metal ions is an aqueous fluid composition that includes acetic acid. The concentration of metal ion in the fluid composition may vary, but ranges from about 2 mM to about 50 mM, such as from about 10 mM to about 20 mM, including from about 20 mM to about 50 mM, in representative embodiments. Likewise, the concentration of acetic acid in the fluid composition may vary, but ranges from about 0.01M to about 0.25M, such as from about 0.05M to about 0.25M, including from about 0.1M to about 0.25M, in representative embodiments.

The uncharged resin and metal ion source that includes metal ions and acetic acid are contacted in a manner such that substantially all of the resultant tetradentate ligand/metal ion complexes have a metal ion complexed to a tetradentate ligand by all four ligands, as described above. In representative embodiments, the uncharged resin is contacted with a fluid composition of metal ion/acetic acid, as described above. The resultant mixture is maintained at a sufficient temperature, e.g., from about 4° C. to about 40° C., such as from about 15° C. to about 25° C., for a sufficient period of time, e.g., from about 5 min to about 180 min.such as from about 20 min to about 60 min, to produce the desired charged resin. Where desired, the reaction mixture may be agitated, e.g., via mixing.

The resultant charged resin is then washed to remove excess metal ion. Any convenient washing protocol may be employed, so long as the protocol preserves the $3^+$ oxidation state of the complexed metal ion in the tetradentate ligand/metal ion complexes of the resin. In representative embodiments, the charged resin is washed with wash fluid comprising acetic acid, where the concentration of acetic acid may vary, but may range from about 0.01M to about 1.0M, such as from about 0.2M to about 0.4M, including from about 0.7M to about 0.9M.

Where desired, e.g., where the resin is to be stored for a period of time prior to use, the charged resin may be stabilized and placed into a storage medium. Any convenient stabilization protocol may be employed, where in a representative embodiment, the resin is contacted with a dicarboxylic acid in a manner sufficient to stabilize the composition. In representative embodiments, the dicarboxylic acid has the formula:

HOOC—(CH$_2$)$_n$—COOH where: n is an integer ranging from about 1 to 10, e.g., an integer ranging from about 2 to 4, such as is present in succinic acid, etc. The concentration of dicarboxylic acid in the stabilization medium contacted with the resin in this step may vary, and may range from about 20 mM to about 200 mM, such as from about 50 mM to about 100 mM.

Where desired, the resultant stabilized resin is combined with a storage medium. Any convenient storage medium may be employed. In certain embodiments, the storage medium is an aqueous solution of a lower alcohol, e.g., ethanol. In representative embodiments, the storage medium is a fluid that ranges from about 10 to about 90% alcohol, such as from about 15 to about 75% alcohol, including from about 20 to about 50% alcohol, e.g., 25% alcohol.

When the resin is prepared and is present in a storage medium, as described above, the resin is stable under standard temperature and pressure conditions for a period of time ranging from about 6 months to about 2 years or longer.

Methods of Using the Phosphoprotein Affinity Resins

The subject phosphoprotein affinity resins find use in a number of different applications, where representative applications include phosphoprotein purification applications. Purification methods provided by the present invention generally include contacting a sample containing or suspected of containing a phosphoprotein(s) with an amount of the subject phosphoprotein affinity resin under conditions which favor binding of the phosphoprotein(s) to the immobilized metal ions of the resin, and then recovering, e.g., via elution, the resultant bound phosphoproteins. One or more washing steps may optionally be included to remove undesired components of the sample contacted to the resin.

The subject methods provide for purification of a phosphoprotein(s) from a sample which contains, in addition to a subject phosphoprotein(s), other components e.g., proteins other than phosphorylated proteins, and other non-protein components such as non-protein macromolecules. The starting sample is any sample containing or suspected of containing a phosphoprotein(s) and one or more other components. In some embodiments, the phosphoprotein of interest is secreted into the culture medium in which cells are grown. In other embodiments, the phosphoprotein remains intracellular (e.g., in the cytoplasm, in a cell membrane, or in an organelle), in which case the cells are disrupted. A variety of protocols for disrupting cells to release an intracellular protein are known in the art, and can be used to extract a phosphoprotein from a cell. Such protocols are found in numerous publications, including, e.g., Current Protocols in Molecular Biology, (F. M. Ausubel, et al., Eds. 1987, and updates). Whether cell culture medium ("culture supernatant") or disrupted cells ("cell lysate") are used as the starting material, the starting material may be subjected to one or more treatments before being applied to a metal ion chelating resin. Such treatments include, but are not limited to, centrifugation, to remove cell debris, etc.; salt precipitation; application to a size exclusion chromatographic column; and application to an ion exchange chromatographic column.

In certain embodiments of interest, a sample is obtained from an initial cellular composition by first combining the initial cellular composition with an amount of an "extraction" buffer. In certain embodiments, the extraction buffer includes an amount of a detergent sufficient to disrupt the formation of protein/protein complexes. The buffer is typically an aqueous composition that includes a suitable amount of a buffering agent, as is known in the art, where representative buffering agents include, but are not limited to: buffers, e.g., Tris-based buffers, borate-based buffers, phosphate-based buffers, imidazole, HEPES, PIPES, MOPS, PIPES, TES, MES and the like. The buffer may include a variety of different types of detergents, including but not limited to, ionic and nonionic detergents. Representative detergents of interest include, but are not limited to: sodium dodecyl sulfate, Tween 20™ and the like. The amount of detergent in the buffer may vary, e.g., depending on the nature of the detergent, but may range from about 0.1% to about 2%, such as from about 1% to about 2%, in representative embodiments. In representative embodiments, the initial cellular composition and buffer are combined in a solid to liquid ratio of about 1:10 to about 1:30, such as about 1:20 to about 1:30. The buffer may include salt such as NaCl, LiCl. The amount of salt in the buffer may vary, but may range from about 0.01M to about 2M, such as from about 0.5M to about 1M.

In these representative embodiments, the initial cellular composition/buffer mixture is then subjected to conditions sufficient to disrupt the cells, e.g., as mentioned above, where representative cell disruption protocols include, but are not limited to, mechanical disruption (e.g., grinding), freezing and thawing, etc., as is known in the art. The resultant cellular debris may then be separated from the remainder of the resultant composition, e.g., via centrifugation, to produce a sample suitable for contact with a phosphoprotein affinity resin of the subject invention.

The conditions under which a sample is contacted to a phosphoprotein affinity resin of the present invention will vary according to various parameters, including the inherent properties of the phosphoprotein, the properties of the undesired components of the sample, etc. Generally, the sample is applied to the phosphoprotein affinity resin under conditions sufficient for binding and immobilization of phosphoproteins present in the sample to the metal ions of the resin, e.g., where the resin may be conveniently present in a column or analogous format, as is known in the art.

In certain embodiments, prior to contact the resin is "equilibrated" as desired by contacting it with a "loading" buffer, where in embodiments of interest the loading buffer includes a buffering agent, as described above, and at least one of: (i) a dicarboxylic acid (e.g., as described below); and (ii) a detergent (e.g., as described above) (iii) a salt. In certain embodiments, the loading buffer includes both of a dicarboxylic acid and a detergent. In certain representative embodiments, the loading buffer is the same as the extraction buffer used for extraction of proteins from an initial cellular sample, as described above. Where the resin is present in a column, this equilibration step is accomplished by running an appropriate amount of the loading buffer solution through the column, where representative amounts include from about 5-10 column volumes.

"Conditions for binding" include a condition of the sample being applied, as well as any equilibration conditions. Conditions may be chosen such that a phosphoprotein retains its native conformation and/or activity. The pH conditions suitable for applying a sample to the phosphoprotein affinity resin range from about 3.5 to about 11, from about 4.0 to about 10.0, from about 4.5 to about 9.5, from about 5.0 to about 9.0, from about 5.5 to about 8.5, from about 6.0 to about 8.0, or from about 6.5 to about 7.5. Temperature conditions suitable for applying a sample to the phosphoprotein affinity resin range from about 4° C. to about 40° C., from about 10° C. to about 30° C., or from about 22° C. to about 25° C.

When the sample contacted with the resin includes phosphoproteins, the above steps result in the production of a resin surface displaying immobilized phosphoproteins. Where desired, the sample contacted resin surface is then washed to remove any non-bound proteins or other sample constituents. One or more washing steps may be included, as desired to remove undesired components. In the broadest sense, the composition and temperature of a washing fluid may vary according to the desired result. Wash fluids may include a buffer, and may further include additional components, as necessary, including, but not limited to, a detergent. In certain embodiments of interest, the sample contacted resin is washed at least once with the same buffer that is employed for extraction of protein from the initial cellular sample and/or equilibration of the resin prior to contact with the sample.

In certain embodiments of interest, the sample contacted resin is also washed with an aqueous buffer composition that includes a dicarboxylic acid. As with the previously described buffer compositions, this dicarboxylic acid containing buffer is typically an aqueous composition that includes a suitable amount of a buffering agent, as is known in the art, where representative buffering agents include, but are not limited to: buffers, e.g., Tris-based buffers, borate-based buffers, phosphate-based buffers, imidazole, HEPES, PIPES, MOPS, PIPES, TES, MES and the like. In representative embodiments, the dicarboxylic acid has the formula:

$$\text{HOOC}-(\text{CH}_2)_n-\text{COOH}$$

wherein n is an integer ranging from about 1 to 10, e.g., an integer ranging from about 2 to 4, such as adipic acid, succinic acid, etc, where in certain embodiments adipic acid is of particular interest. The concentration of the dicarboxylic acid in the wash solution may vary, and may range from about 20 mM to about 200 mM, such as from about 50 mM to about 100 mM. In certain embodiments, this wash fluid may be the same as the extraction and loading buffers.

Where desired, the resultant resin immobilized phosphoprotein can be separated, e.g., eluted, from the resin, e.g., using a pH gradient; addition of a competitor, e.g., an organic acid, phosphates; addition of a displacer such as phosphate; and the like, to produce a fluid composition enriched for phosphoprotein, as compared to the initial cellular source, as well as sample contacted with the resin. In certain embodiments, elution of the captured phosphoproteins is accomplished by contacting the resin with a sufficient amount and for a sufficient period of time with a phosphate buffer, where these amounts and times are readily determined by those of skill in the art.

Using the above-described method, phosphoproteins in a sample can be purified to a desired degree, depending on the application. In some embodiments, a phosphoprotein purified composition produced by the subject method is at least about 60%, at least about 70%, at least about 80%, at least about 85%, at least about 90%, at least about 95%, at least about 98%, at least about 99%, or more, pure, e.g., free of macromolecules other than the polypeptide found in a sample comprising the polypeptide before the polypeptide is purified. Purity can be determined using any known method, including, but not limited to, SDS-PAGE separation following by staining (e.g., Coomassie blue, silver staining, etc.), SDS-PAGE followed by transfer to membrane for Western blots with phosphoprotein specific antibodies.

The recovery of the phosphoprotein (e.g., the yield) is, in certain representative embodiments, at least about 30%, at least about 40%, at least about 50%, at least about 60%, at least about 70%, at least about 75%, at least about 80%, at least about 85%, at least about 90%, at least about 95%, at least about 98%, or more, where recovery is determined using the protocol described in Protein assay using bicinchoninic acid (Anal Biochem. 1989, 180, 136-139; Brown et al), Phosphate estimation using alkaline hydrolysis and malachite green (Anal Biochem, 1993, 214, 138-141, Ekman et al).

A feature of the subject methods is that the above purification protocol can be run in a period of less than about 5 hours, including less than about 4 hours, such as in about 3 hours or even 2 hours or less, on a variety of different types of cellular and tissue samples.

Another feature of the subject methods is that the phosphoprotein affinity resin is highly specific for phosphoproteins, i.e. proteins having one or more phosphorylated amino acid residues, such as phosphorylated serine, tyrosine and/or threonine residues. A given method is considered to be highly specific for phosphoproteins if, when contacted with a sample that includes both phosphoproteins and non-phosphorylated protein in a separation protocol (as described in the Experimental protocol below), substantially no non-phosphorylated proteins are captured on the resin, while phosphoproteins are captured on the resin, as determined using the protocol described in the Experimental section, below.

In addition to the above-described representative phosphoprotein enrichment protocols, under appropriate conditions the subject phosphoprotein affinity resins may also find use in IMAC affinity peptide tagged protein purification protocols, such as those described in U.S. Pat. Nos.: 4,569,794; 5,047,513; 5,284,933; 5,310,663; 5,962,641; 5,594,115; and 6,242,581; the disclosures of which are herein incorporated by reference, as well as the purification and analyte detection applications described in U.S. Pat. No. 6,703,498; the disclosure of which is herein incorporated by reference.

As summarized above, also provided are kits and systems for use in practicing the subject methods. The kits and systems at least include the subject phosphoprotein affinity resins, as described above. The kits and systems may also include a number of optional components that find use in the subject methods. Optional components of interest include buffers, including extraction/loading/washing buffer or buffers (e.g., as described above), and the like.

In certain embodiments of the subject kits, the kits will further include instructions for practicing the subject methods or means for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

The following examples are offered by way of illustration and not by way of limitation.

EXPERIMENTAL

I. Protocol for Preparation of CM-Asp Beads

A. Wash 100 ml of Superflow 6 resin (Sterogene Bioseparations, cat# 806-01) with Milli Q water to remove ethanol.

B. Epoxy activation of Superflow 6

Remove excess water from the beads by vacuum filtration. 100 g of suction-dried Superflow 6 is transferred to 1 L conical flask. 15 mL of Epichlorohydrin is added followed by 100 mL of 2M NaOH containing 600 mg of $NaBH_4$. The mixture is left on an orbital shaker at RT. After 4 hours fresh 10 mL of epichlorohydrin are added to the mixture and the reaction is allowed to proceed for total of 20 hours.

C. Coupling of aspartic acid

The Epoxy-activated superflow is washed extensively with Milli Q water until the pH of flow through is same as pH of water and then suction dried. Dissolve 6 g NaOH in 150 mL $H_2O$ with mechanical stirring in a 250 ml flask. Cover solution and place in refrigerator to cool overnight. Remove NaOH solution from refrigerator and place in an ice bath. Add 14.0 g L-aspartic acid (MW 133.1) in with stirring, followed by 22 g sodium carbonate (MW 106) with stirring. Monitor the temperature & if temperature is higher than 25° C., cool to 25° C. in an ice bath. Adjust the pH to the range 11.0-11.1 by the addition of conc. NaOH or conc. HCl. Transfer the washed and suction dried resin to the flask. Transfer Aspartic acid solution to the flask and mix on an orbital shaker at ambient for 16 hours. The gel is washed with Milli Q water until the pH of washes is same as pH of water.

D. Carboxy-methylation

The Asp-superflow 6 is carboxymethylated. Wash Aspartate-Superflow with 1×700 mL 10% $Na_2CO_3$. Suction dry. Dissolve 11.25 g NaOH in 150 mL $H_2O$ with mechanical stirring in a 250 ml flask. Cover solution and place in refrigerator to cool overnight. Remove NaOH solution from refrigerator and place in an ice bath. Add 37.5 g bromoacetic acid (MW 139) in 7.5 g increments, with stirring. Monitor temperature of solution during the addition; the temperature should be no higher than 30° C. at the end of the addition. Before proceeding, test the pH of the solution. If the pH is <7, add NaOH pellets, 0.5 g at a time, being careful not to let the temperature exceed 30° C., until the solution pH is >7. Carefully add 8.25 g $Na_2CO_3$ (MW 106) with stirring, and remove the ice bath; the $Na_2CO_3$ will go completely into solution as the solution warms. Adjust pH to the range 10.0-10.1 with conc. HCl or conc. NaOH, using a standardized pH meter. Transfer the washed and suction dried resin to a conical flask. Transfer bromoacetic acid solution to the flask and mix at ambient for at least 43 hours. Collect resin by filtration. Wash thoroughly with 6×100 mL MilliQ water, 1×700 mL 10% acetic acid, and 18×100 mL Milli Q water. Wash the gel with with Milli Q water until the pH of washes is same as pH of water. Suction dry the resin. The resin can then either be charged with metal ion immediately or stored in 25% ethanol.

II. Charging of Resin with Metal Ion 20 ml of the final resin produced in Example I, above, is charged with 200 mL of freshly prepared 20 mM $FeCl_3$ and 100 mM acetic acid in Milli Q water for 10 min, washed multiple times with Milli Q water (care must be take to minimize exposure of $FeCl_3$ solution to air). The Fe charged resin is mixed with a solution of either 200 ml of 100 mM succinic acid, pH 5.5 or 200 ml of 5% acetic acid solution for 1 hour. Resin is washed multiple times with Milli Q water and then stored in 25% Ethanol.

III. Use of Affinity Resin in Phosphorylated Protein Enrichment Applications

A) Protocol for running samples on phosphoprotein column

Extraction/loading Buffer:

50 mM MES, 500 mM NaCl, 100 mM Adipic acid, 1% NP-40, pH 6.0

Elution buffer:

20 mM sodium phosphate ($Na_2HPO_4 \cdot 7H_2O$), 500 mM NaCl, pH 7.2

Proteins were extracted form cells by resuspending the cell pellet in extraction buffer and incubating the suspension at 4° C. for 10 min. Cell extract was centrifuged at 10,000×g for 20 min at 4° C. to pellet any insoluble material. The supernatant was transferred to a clean tube and this was the cell lysate or sample used for the experiment.

Column with 1 ml of phosphoprotein resin was washed with water to get rid of storage buffer and equilibrated with 5 ml of loading buffer. The cell lysate collected above was loaded on the column (a small portion of the cell lysate was retained for protein assay and other analysis). The column with sample was gently agitated at 4° C. for 20 min on a platform shaker.

Flow through was collected and the column washed with loading buffer to remove any non-adsorbed proteins. Phosphoproteins were eluted using elution buffer.

B) Results for enrichment of phosphoproteins from different cell extracts

To check for specific binding of phosphoproteins, cell extracts from different cell lines and from chicken muscle were run on the Phosphoprotein Resin, with $Fe^{3+}$ loading in 100 mM Acetic acid and washed with 5% acetic acid, according to the protocol given above (III A)

| Cell line | Original sample (Protein loaded, mg) | Flow-through (Protein, not bound, mg) | Eluate (protein bound, mg) | Eluate (% of total protein loaded) |
| --- | --- | --- | --- | --- |
| HEK 293 | 2.72 | 2.08 | 0.224 | 8% |
| Jurkat | 2.93 | 2.61 | 0.238 | 8% |
| COS-7 | 1.76 | 1.55 | 0.151 | 9% |
| NIH 3T3 | 3.83 | 3.48 | 0.301 | 8% |
| Hela | 2.29 | 2.02 | 0.182 | 8% |

Pierce BCA protein assay (cat#23235) was used for protein quantitation.

Samples were analyzed by western blotting using some Phosphoprotein-specific antibodies. Phosphoproteins were detected in the eluates, providing evidence that the above resin has high affinity for binding phosphoproteins.

Figure 1:
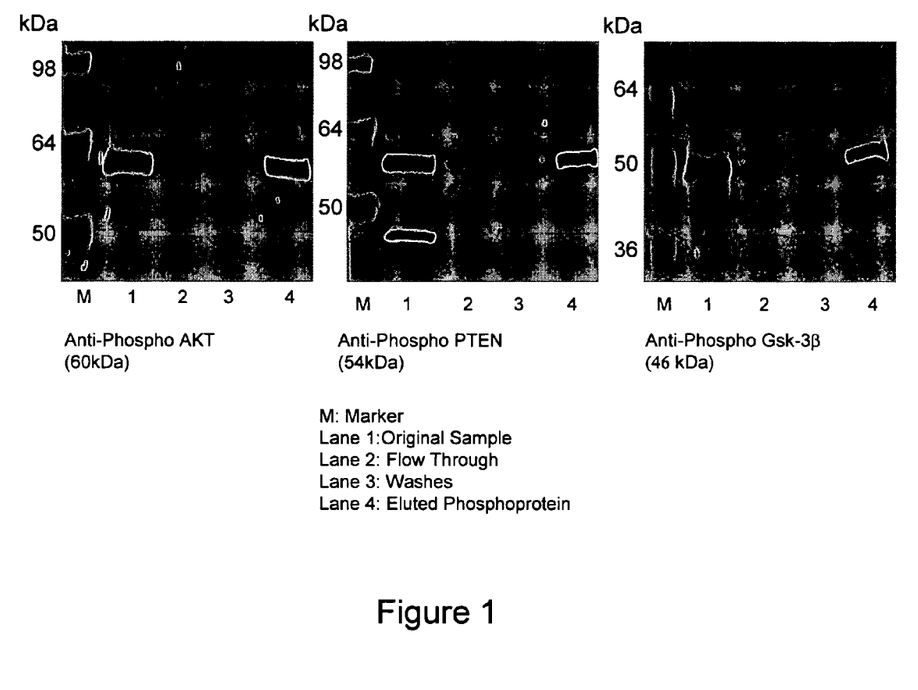
FIG. 1. Western blot data for phosphoproteins from HEK 293 enriched using Phosphoprotein resin and buffers given in protocol for running sample on Phosphoprotein column. Samples from the column were analyzed by western blotting using phosphoprotein specific antibodies. Phosphorylated proteins were clearly detected in the eluate fraction.

Representative western blot data for HEK 293 cells with three different antibodies is given below.

C) Specificity of the Resin

Phosphoproteins besides having phosphate group can also have clusters of carboxylic amino acids. These carboxylic group clusters, when present can lead to non-specific binding, as Ferric has affinity for binding to these groups besides the phosphate groups.

Phosphoprotein Resin (Resin charged with Fe) has been treated with organic acids, succinic acid or acetic acid prior to running phosphoprotein samples to eliminate the nonspecific binding of carboxylic group clusters.

Non-phosphorylated protein, which has clusters of carboxylic amino acids was run under the same conditions on two different Ferric charged resin, treated with either succinic acid or acetic acid to check for non-specific binding.

Resin 1: Resin with $Fe^{3+}$ loading in water, washed with succinic acid

Resin 2: Resin with $Fe^{3+}$ loading in 100 mM Acetic acid, washed with 5% acetic acid.

Column was run according to the protocol for Enrichment of Phosphoprotein (section IIIA).

| Resin | Original sample | Flow through | Eluate |
| --- | --- | --- | --- |
| Resin 1(succinic acid) | 3.18 mg | 2.99 mg | 0.174 mg |
| Resin 2(Acetic acid) | 3.18 mg | 3.12 mg | 0.010 mg |

Original sample: Total amount of protein loaded on the column

Flow-through: Total amount of protein that did not bind to the column

Eluate: Total amount of protein that bound to the column and was recovered with elution As seen from the above results, Resin 1 bound nonphosphorylated protein with clusters of carboxylic amino acids, 0.174 mg (5.5% of total protein loaded on the column; 0.174/3.18)

Resin 2 had negligible binding of the same, 0.010 mg (0.3% of total protein loaded on the column; 0.010/3.18)

Resin with $Fe^{3+}$ loading in 100 mM Acetic acid, washed with 5% acetic acid has almost no non-specific binding under the current experimental conditions (protocol IIIA). This resin is much more specific than the resin with $Fe^{3+}$ loading in water, washed with succinic acid.

D) Specific, optimized binding and elution of phosphopeptides

Figure 2:
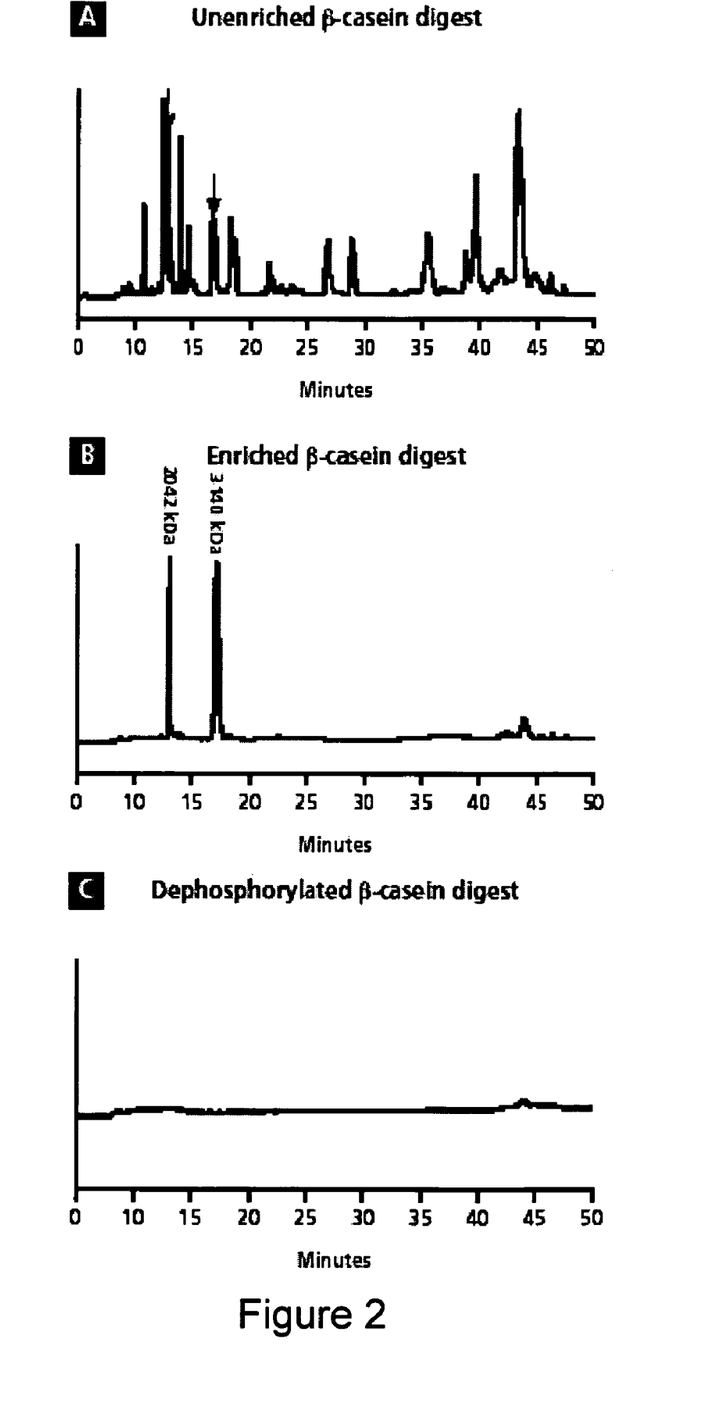
FIG. 2. Purification of phosphopeptides of trypsin-digested β-casein using the phosphoprotein resin of the invention. Reverse phase HPLC (RP-HPLC) data is shown for crude protein digest (Panel A), eluate (purified phosphopeptides; Panel B) and eluate of a dephosphorylated sample (Panel C).

To demonstrate the specificity of the phosphoprotein resins of the invention for phosphopeptides, we analyzed β-casein protein samples digested with trypsin by reverse phase HPLC.

β-casein protein was digested with trypsin (sequencing grade). Protein digest was diluted at a ratio of 1:1 with Loading Buffer (250 mM acetic acid, pH 2.5-3.5) and run on a phosphoprotein column of the invention. The bound fraction was eluted with Elution Buffer then freeze-dried and reconstituted in 0.1% TFA in water (v/v). Reverse phase HPLC (RP-HPLC) data is shown for crude protein digest (Panel A), eluate (purified phosphopeptides; Panel B) and eluate of a dephosphorylated sample (Panel C). The eluted fractions were separated by RP-HPLC on an XTerra RP18 column (5 µm, 4.6×150 mm) with UV detection at 215 nm (Solvent A: 0.1% TFA in water [v/v], Solvent B: 0.1% TFA in acetonitrile [v/v]). The two phosphopeptide fractions collected in Panel B were analyzed by MALDI.

As can be seen from the data in FIG. 1, the phosphoprotein resin of the invention specifically bound the phosphorylated peptides from trypsin digested β-casein (panels A and B). The specificity of this binding was confirmed by dephosphorylating β-casein prior to phosphoprotein resin enrichment, which resulted a marked reduction in the peptides bound to the resin (Panel C).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of making a phosphoprotein affinity resin, said method comprising:
   (a) contacting an uncharged aspartate-based resin with a metal ion source comprising metal ions having a $3^+$ oxidation state and having selective affinity for phosphorylated amino acids to produce a metal ion charged aspartate-based resin, wherein said aspartate-based resin comprises a tetradentate ligand and said contacting occurs in the presence of acetic acid; and
   (b) removing non-complexed metal ion from said charged aspartate-based resin to produce said phosphoprotein affinity resin.

2. The method according to claim 1, wherein said metal ion source comprises $Fe^{3+}$.

3. The method according to claim 1, wherein said metal ion source comprises lanthanide ion.

4. The method according to claim 3, wherein said metal ion source comprises $Eu^{3+}$.

5. The method according to claim 1, wherein said aspartate-based resin is synthesized from an aspartic acid.

6. The method according to claim 5, wherein said aspartate-based resin is an alkylated aspartate-based resin.

7. The method according to claim 6, wherein said alkylated aspartate-based resin is a carboxymethylated aspartate-based resin.

8. The method according to claim 1, wherein said method further comprises contacting said phosphoprotein affinity resin with a dicarboxylic acid to produce a stabilized phosphoprotein affinity resin.

9. The method according to claim 8, wherein said dicarboxylic acid has the formula:

$$HOOC-(CH_2)_n-COOH$$

wherein:
   n is an integer ranging from about 1 to 10.

10. The method according to claim 9, wherein n is an integer ranging from about 2 to about 4.

11. The method according to claim 8, wherein said stabilized phosphoprotein affinity resin is combined with an aqueous solution of a lower alcohol to produce a storage stable composition of said stabilized phosphoprotein affinity resin.

* * * * *